(12) United States Patent
Nakagawa et al.

(10) Patent No.: US 9,010,171 B2
(45) Date of Patent: Apr. 21, 2015

(54) EXHAUST GAS ANALYZING APPARATUS, EXHAUST GAS ANALYZING SYSTEM AND METHOD OF OPERATING THE SAME

(71) Applicant: HORIBA, Ltd., Kyoto (JP)

(72) Inventors: Hiroyoshi Nakagawa, Kyoto (JP); Koji Watanabe, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 0 days.

(21) Appl. No.: 13/898,712

(22) Filed: May 21, 2013

(65) Prior Publication Data

US 2013/0312486 A1    Nov. 28, 2013

(30) Foreign Application Priority Data

May 23, 2012  (JP) .................................. 2012-118096
Nov. 6, 2012  (JP) .................................. 2012-244284

(51) Int. Cl.
  *G01N 25/00*  (2006.01)
  *G01M 15/10*  (2006.01)
  *G01N 1/22*   (2006.01)

(52) U.S. Cl.
  CPC ........... *G01M 15/102* (2013.01); *G01N 1/2252* (2013.01); *G01N 2001/2261* (2013.01)

(58) Field of Classification Search
  CPC .................................................. G01N 27/407
  USPC ........................................................ 73/23.31
  See application file for complete search history.

(56) References Cited

U.S. PATENT DOCUMENTS 4,193,963 A  *  3/1980  Bruening et al. ................ 422/52

FOREIGN PATENT DOCUMENTS

| JP | 60209165 A   | 10/1985  |
| JP | 61265562 A   | 11/1986  |
| JP | 2002071524   | 3/2002   |
| JP | 2002071527 A | 3/2002   |
| JP | 2003028765 A | 1/2003   |
| JP | 2010276473   | 12/2010  |
| JP | 2012-002799  | 1/2012   |

* cited by examiner

*Primary Examiner* — Laura Martin
*Assistant Examiner* — Alex Devito
(74) *Attorney, Agent, or Firm* — Brooks Kushman P.C.

(57) ABSTRACT

An exhaust gas analyzing apparatus includes analyzer main bodies, exhaust gas introducing parts for guiding the exhaust gas from an exhaust pipe, through which the exhaust gas passes, to the analyzer main body, heaters for heating the analyzer main bodies and the exhaust gas introducing parts, respectively, and a temperature regulating mechanism for controlling the heaters to regulate temperatures of the analyzer main bodies and the exhaust gas introducing parts, and a first mode which has the temperature regulating mechanism regulate the temperatures of the analyzer main body and the exhaust gas introducing part to an analyzable temperature that is a predetermined temperature allowing a start of analysis of the exhaust gas, or a second mode which has the temperature regulating mechanism regulate the temperature of the analyzer main body to the analyzable temperature and turning off the heater for the exhaust gas introducing part can be selected.

8 Claims, 10 Drawing Sheets

| HEATING MODE | HEATER | | HOT HOSE | |
|---|---|---|---|---|
| | FOR ANALYZING UNIT | FOR SAMPLING PART | FOR EXHAUST GAS INTRODUCTION PIPE | FOR CONNECTION PIPE |
| OFF | × | × | × | × |
| SLEEP | ○ | × | × | × |
| PAUSE | ○ | △ | △ | △ |
| STANDBY | ○ | ○ | ○ | ○ |

×: NO HEATING
△: HEATING TO ABOUT 100°C
○: HEATING TO ABOUT 191°C

FIG.3

EXHAUST GAS ANALYZING APPARATUS, EXHAUST GAS ANALYZING SYSTEM AND METHOD OF OPERATING THE SAME

CROSS-REFERENCE TO RELATED APPLICATIONS

This application claims priority to JP Application No. 2012-118096, filed on May 23, 2012, and JP Application No. 2012-244284, filed on Nov. 6, 2012, the disclosures of which are incorporated in their entirety by reference herein.

TECHNICAL FIELD

The present invention relates to an exhaust gas analyzing apparatus for measuring exhaust gas discharged from an internal combustion engine of an automobile and the like. The present invention also relates to an exhaust gas analyzing system for the internal combustion engine and a method of operating the system, and is characterized by especially an operation at start-up.

BACKGROUND ART

To measure exhaust gas discharged from the internal combustion engine of the automobile and the like, according to a conventional method, a vehicle mounted on a chassis dynamo apparatus is traveled according to a predetermined travelling mode by an automatic operating robot, discharged exhaust gas is collected by a constant-volume sampling device, and the collected sample gas is supplied to an exhaust gas analyzing apparatus equipped with a plurality of different gas analyzers having different measurement principles, and is measured for each component.

Each of the gas analyzers mounted in the exhaust gas analyzing apparatus includes heating equipment such as a hot hose and a heater, and at measurement, a main body of the gas analyzer and an exhaust gas introduction line are heated to respective analyzable temperatures predetermined according to specifications.

However, it is unsuitable to heat them to the respective predetermined analyzable temperatures during operations other than analysis in terms of costs. For this reason, the conventional apparatuses are configured such that the heating state can be switched among three following phases: (1) an "OFF mode" in which both the gas analyzer main body and the exhaust gas introduction line are not heated, (2) a "pause mode" in which the gas analyzer main body is regulated to have an analyzable temperature of about 191° C., and the exhaust gas introduction line is regulated to have a predetermined intermediate temperature (about 100° C.) that is lower than the analyzable temperature, and (3) a "standby mode" in which both of the gas analyzer main body and the exhaust gas introduction line are regulated to have the analyzable temperature.

However, from the viewpoint of the recent severe energy supply situation and environmental load, it has been demanded to regulate the heating state more finely. Nevertheless, once heating of the gas analyzer main body is stopped and its temperature lowers, even when heating is restarted and the temperature returns to the initial value, it takes time for the analyzer main body to be stably put into an analyzable state without any drift. Specifically, when the heating state is switched from the "OFF mode" to the "standby mode", it takes at least six hours to regain a stable state.

A plurality of analyzing units and an exhaust gas sampling line, which constitute the exhaust gas analyzing system of the internal combustion engine, each are further equipped with a temperature regulating mechanism formed of a hot hose, a heater, or the like, and at analysis, temperatures of the analyzing units and the exhaust gas sampling line are kept to a specified analyzing temperature (for example, about 191° C.) according to the specifications.

As described above, the specified analyzing temperature is substantially high, and it takes a long time (for example, a few hours in the case of starting at normal temperatures) to stably attain the specified analyzing temperature from a start of the operation of the temperature regulating mechanism.

Some analyzing units such as a hydrogen flame ionization detector and a chemiluminescent NO meter may require dedicated gas (analyzing gas) for analysis of the exhaust gas. For example, to analyze the exhaust gas, the hydrogen flame ionization detector requires hydrogen gas, and the chemiluminescent NO meter requires ozone gas.

In such analyzing units, in addition to temperature stabilization, for example, stabilization of the flow rate of the analyzing gas and purge of inside remaining gas are needed and thus, unless a predetermined time (for example, a few dozen minutes) elapses from a start of the introduction of the analyzing gas, the stable analyzing operation cannot be performed.

Accordingly, to attain the state in which exhaust gas analysis can be immediately started (hereinafter referred to as standby mode), at least, it is necessary to operate the temperature regulating mechanism in advance to attain the specified analyzing temperature, and start the introduction of the analyzing gas to keep the analyzing units in the stably-operable state.

Thus, conventionally, the operations of the temperature regulating mechanism and the introduction of the analyzing gas are simultaneously started and then, proceed in parallel, thereby reducing the time required to attain the standby mode.

For example, JPA 2002-71524 describes a scheduler for automatically setting operation timings of the exhaust gas analyzing apparatus and the dynamo, which are used in an automobile test, to efficiently spend time for the test. When receiving a command of standby mode from the scheduler, the exhaust gas analyzing apparatus starts the operation of the temperature regulating mechanism and the introduction of the analyzing gas at the same time.

However, since a temperature stabilizing time taken by the temperature regulating mechanism is generally longer than a time that elapses before the analyzing units become stably operable from the start of the introduction of the analyzing gas, during a time elapses before the temperature becomes stable after the analyzing units become stably operable, the analyzing units are in a waiting state in despite of the introduction of the analyzing gas, uselessly consuming the analyzing gas.

SUMMARY

Technical Problem

Thus, the present invention intends to provide an exhaust gas analyzing apparatus capable of achieving further energy saving and rapidly starting analysis. The present invention also provides an exhaust gas analyzing system capable of achieving further energy saving.

Solution to Problem

That is, an exhaust gas analyzing apparatus according to a first aspect of the present invention includes an analyzer main body for analyzing exhaust gas; an exhaust gas introducing part for guiding the exhaust gas from an exhaust pipe passing the exhaust gas therethrough to the analyzer main body; a heater for heating the analyzer main body and a heater for heating the exhaust gas introducing part; and a temperature regulating mechanism for controlling the heaters to regulate temperatures of the analyzer main body and the exhaust gas introducing part, wherein a first mode which has the temperature regulating mechanism regulate the temperatures of the analyzer main body and the exhaust gas introducing part to an analyzable temperature that is a predetermined temperature allowing a start of analysis of the exhaust gas, or a second mode which has the temperature regulating mechanism regulate the temperature of the analyzer main body to the analyzable temperature and turning off the heater for the exhaust gas introducing part can be selected. According to the present invention, the term "OFF" means the substantial OFF state, and includes a state in which a minute waiting current flows.

With such configuration, the temperature regulating mechanism can select the second mode of regulating the temperature of the analyzer main body to the analyzable temperature and turning off the heater for the exhaust gas introducing part. Therefore, further energy saving can be achieved as compared to the conventional "pause mode". In addition, by reheating the exhaust gas introducing part, the state can be rapidly shifted to the analyzable state.

According to the present invention, a third mode which has the temperature regulating mechanism regulate the temperature of the analyzer main body to the analyzable temperature, and the exhaust gas introducing part to an intermediate temperature as a predetermined temperature, the predetermined temperature being lower than the analyzable temperature can further be selected.

A fourth mode which has the temperature regulating mechanism turn off all of the heaters can further be selected.

An exhaust gas analyzing system according to a second aspect of the present invention includes one or more analyzing units for analyzing exhaust gas sampled from an exhaust pipe of an internal combustion engine while using analyzing gas other than the exhaust gas; and a temperature regulating mechanism for regulating a temperature of the analyzing units and/or an exhaust gas sampling line, and prior to analysis of the exhaust gas, introduction of the analyzing gas is started with a delay of predetermined time from the start of the operation of the temperature regulating mechanism.

The start of the operation of the temperature regulating mechanism is not limited to the start of the operation from power-on, and for example, includes the start of the temperature regulating operation from a predetermined state where the intermediate temperature is maintained toward a target stable temperature.

To minimize consumption of the analyzing gas and power consumption of the temperature regulating mechanism prior to the standby mode, preferably, prior to the start of the analysis of the exhaust gas, the introduction of the analyzing gas is started with a delay of predetermined time from the operation start time point of the temperature regulating mechanism such that a temperature stabilizing time point as a time point when the temperature regulated by the temperature regulating mechanism reaches a predetermined stable temperature range for the first time after the start of the operation of the temperature regulating mechanism substantially coincides with an analyzable time point as a time point when the analyzing units can start stable analysis for the first time after the start of the introduction of the analyzing gas.

A specific embodiment includes one or more analyzing units for analyzing exhaust gas sampled from an exhaust pipe of an internal combustion engine while using analyzing gas; a temperature regulating mechanism for regulating a temperature of the analyzing units and/or an exhaust gas sampling line; a temperature stabilizing time point acquiring part for acquiring a temperature stabilizing time point as a time point when the temperature regulated by the temperature regulating mechanism reaches a predetermined stable temperature range for the first time after the start of the operation of the temperature regulating mechanism; a stable-operation required time storing part for storing a stable-operation required time as a required time taken until the analyzing units are put into a predetermined stable state allowing the units to start stable analysis for the first time after the start of introduction of the analyzing gas; and a control part for, prior to the start of the exhaust gas analysis, operating the temperature regulating mechanism, acquiring the temperature stabilizing time point from the temperature stabilizing time point acquiring part, acquiring the stable-operation required time from the stable-operation required time storing part, and calculating an introduction start time point of the analyzing gas such that a stable-analysis enabling time point when the analyzing units can start stable analysis for the first time after the start of the introduction of the analyzing gas substantially coincides with the temperature stabilizing time point.

Specific examples of the analyzing units include a hydrogen flame ionization detector using hydrogen gas as the analyzing gas and a chemiluminescent NO meter using ozone as the analyzing gas.

The exhaust gas analyzing system according to the second aspect of the present invention includes one or more analyzing units for analyzing exhaust gas sampled from an exhaust pipe of an internal combustion engine while using analyzing gas; and a temperature regulating mechanism for regulating a temperature of the analyzing units and/or an exhaust gas sampling line, and prior to the start of the analysis of the exhaust gas, an operation start time point of the temperature regulating mechanism and an introduction start time point of the analyzing gas are set such that a temperature stabilizing time point as a time point when the temperature regulated by the temperature regulating mechanism reaches a predetermined stable temperature range for the first time after the start of the operation of the temperature regulating mechanism substantially coincides with an analyzable time point as a time point when the analyzing units can start stable analysis for the first time after the start of the introduction of the analyzing gas.

With such configuration, in the case where the temperature stabilizing time obtained by the temperature regulating mechanism is longer than time needed until the analyzing units can start to stable operate after the start of the introduction of the analyzing gas and vice versa, the operation start time point of the temperature regulating mechanism can be substantially coincided with the introduction start time point of the analyzing gas, achieving the same effect.

Advantageous Effects of Invention

According to the first aspect of the present invention, since further energy saving can be achieved, and the temperature of the analyzer main body is kept at the analyzable temperature at all times to maintain the analyzable state, analysis can be rapidly performed merely by reheating the exhaust gas introducing part, resulting in efficient exhaust gas analysis.

According to the second aspect of the present invention, since time when the analyzing units wait until the temperature becomes stabilized while the analyzing gas is introduced can be shortened than conventional technique, consumption of the analyzing gas can be reduced.

BRIEF DESCRIPTION OF THE DRAWINGS

FIG. 3 is a table showing various heating modes in the embodiment;

DESCRIPTION OF EMBODIMENTS

<First Aspect of the Present Invention>

An embodiment of the present invention will be described below with reference to figures.

Figure 1:
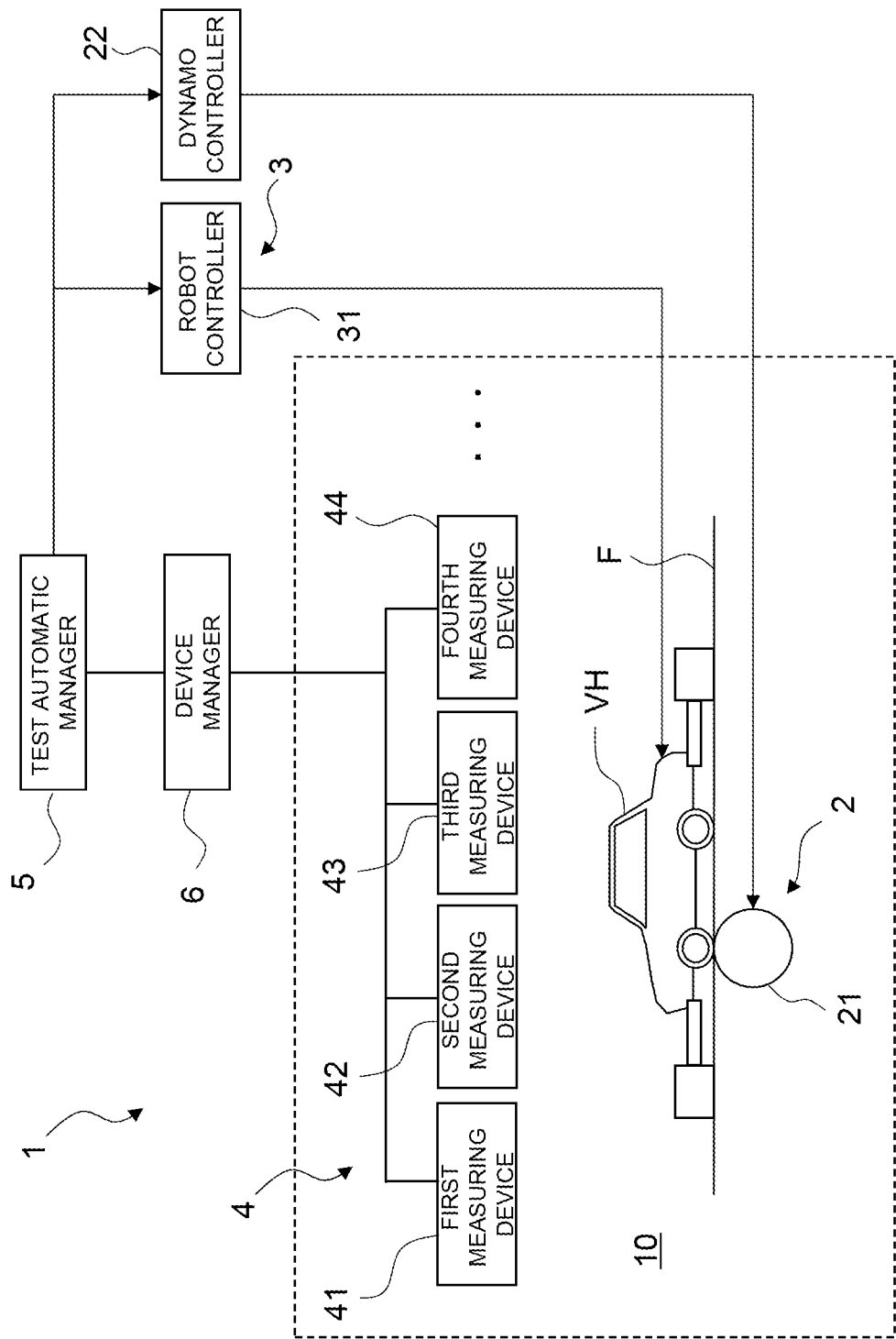
FIG. 1 is a schematic overall view showing an exhaust gas analyzing system in accordance with an embodiment of a first aspect of the present invention.

FIG. 1 schematically shows an entire exhaust gas analyzing system 1 in accordance with this embodiment. The exhaust gas analyzing system 1, as shown in this figure, includes a chassis dynamometer 2, an automatic driving device 3, a test automatic manager 5, a plurality of exhaust gas measuring devices 4, and a device manager 6. A vehicle VH can be traveled on the chassis dynamometer 2 in a pseudo manner, and performances of the vehicle VH, such as fuel consumption and exhaust gas components, can be tested.

Each of the parts will be described below. The chassis dynamometer 2 includes a uniaxial rotating drum 21, a motor and a flywheel (not shown) that apply loads on the rotating drum 21, and a dynamo controller 22 for controlling them. The rotating drum 21 and the motor or the flywheel are placed in a pit below a floor F of a test chamber 10, and a top of the rotating drum 21 is exposed from an opening formed on the floor F of the test chamber 10. Driving wheels of the vehicle VH are located at test positions immediately above the top of the rotating drum 21 such that the vehicle VH can travel as if it actually travels. The dynamo controller 22 is accommodated in a measurement chamber provided, for example, adjacent to the test chamber 10. The test chamber 10 and the measurement chamber (and the pit) are collectively referred to as a cell.

The automatic driving device 3 includes a driving robot (not shown) that is mounted in a cabin of the vehicle VH and drives an accelerator, a brake, and a clutch, and a robot controller 31 that is connected to the driving robot and controls the driving robot, and the automatic driving device 3 sends various command signals to the robot controller 31, thereby controlling the driving robot to cause the vehicle VH to automatically travel in one or more travelling modes such as a 10 mode and a LA mode. The robot controller 31 is accommodated in, for example, the measurement chamber.

Though not described in detail, the test automatic manager 5 basically serves to set a schedule of a travelling test. Examples of setting the schedule of the travelling test include setting of a test mode and a test date, more detailed setting of vehicle behaviors such as vehicle speed and engine rotating speed, and setting of a measurement target and measurement timing. The test automatic manager 5 is provided with a communication port, and the measuring devices 4, the chassis dynamometer 2, and the automatic driving device 3 are connected to the test automatic manager 5 so as to be intercommunicable in a wired or wireless manner.

When the operator sets the schedule in this manner, the test automatic manager 5 appropriately transmits the command signal to the chassis dynamometer 2, the automatic driving device 3, and the device manager 6 according to the schedule, and controls them such that the test is made as scheduled.

Although one device manager 6 is connected to the test automatic manager 5 in FIG. 1, a plurality of device managers 6 may be connected to the test automatic manager 5. In this case, the test automatic manager 5 can perform scheduling for each of the device managers 6.

The exhaust gas measuring devices 4 (hereinafter also referred to as merely measuring devices 4) are devices used to measure the exhaust gas, and include, for example, a device configured of one or more gas analyzers as unit equipment to measure exhaust gas components, and a device such as a constant-volume sampling device that makes pretreatment of measuring exhaust gas components.

In this embodiment, plural types of measuring devices 4 are adopted. For example, a first measuring device 41 including a plurality of different gas analyzers having different measurement principles, a second measuring device 42 as a constant-volume sampling device, a third measuring device 43 as an EGR rate measuring device, and a fourth measuring device 44 as an ultrasonic flow rate meter are provided. Examples of the gas analyzer include an FID for measuring THC, a CLD for measuring $NO_x$, and an NDIR for measuring $CO$ and $CO_2$.

Figure 2:
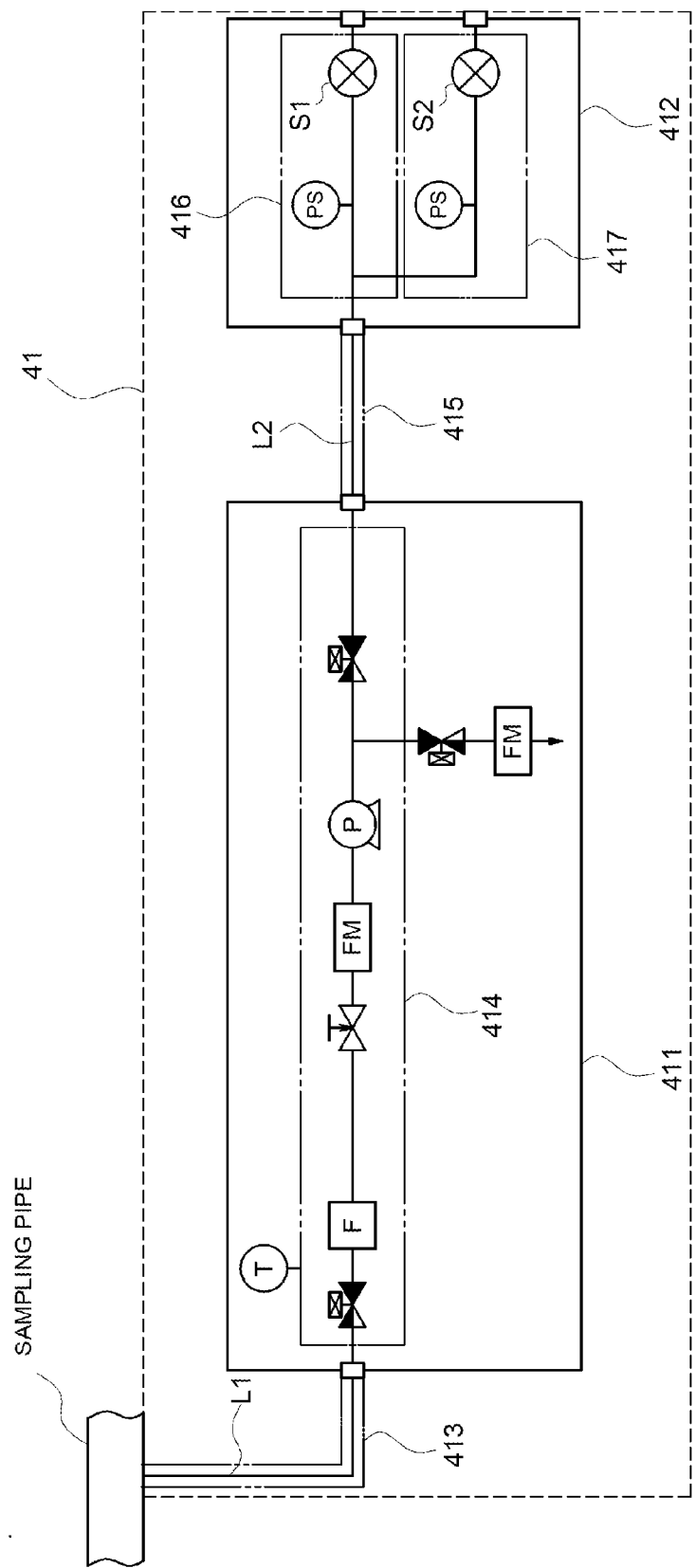
FIG. 2 is a fluid circuit diagram of a first measuring device (exhaust gas analyzing apparatus) in the embodiment.

As shown in FIG. 2, the first measuring device 41 includes an analyzing part 412 including one or more types of gas analyzers S1, S2 and a sampling part 411 for sampling exhaust gas from a sampling pipe connected to an exhaust pipe of the vehicle VH via an exhaust gas introduction pipe L1, and the sampling part 411 is connected to the analyzing part 412 via a connection pipe L2. The gas analyzers S1, S2 in FIG. 2 are hydrogen flame ionization detectors.

In the first measuring device 41, the exhaust gas introduction pipe L1 and the connection pipe L2 are provided with hot hoses 413, 415 for heating the pipes to predetermined temperatures, respectively, and the sampling part 411 and the analyzing part 412 are provided with heaters 414, 416, and 417 for heating their internal equipment and internal flow paths to respective predetermined temperatures. In this embodiment, targets to be heated are heated by the hot hoses 413, 415 and the heaters 414, 416, and 417 to about 191° C. as the analyzable temperature.

As shown in FIG. 3, the hot hoses 413, 415 and the heaters 414, 416, and 417 are configured to be in one of four types of heating modes: an "OFF mode", a "sleep mode", a "pause mode" and a "standby mode". In the "OFF mode", all of the hot hoses 413, 415 and the heaters 414, 416, and 417 are not operated. In the "sleep mode", the heaters 416, 417 for the analyzing part 412 is regulated to have the analyzable temperature (about 191° C. in this embodiment), and the hot hoses 413, 415 and the heater 414 for the sampling part 411 are not operated. In the "pause mode", the heaters 416, 417 for the analyzing part 412 are regulated to have the analyzable temperature, while the hot hoses 413, 415 and the heater 414 for the sampling part 411 are regulated to have the predetermined intermediate temperature (about 100° C. in this embodiment) that is lower than the analyzable temperature. In the "standby mode", all of the hot hoses 413, 415 and the heaters 414, 416, and 417 are regulated to have the analyzable temperature (about 191° C. in this embodiment).

Each of the devices 4 includes a sensor for measurement and a local computer built-in, and the local computer functions as a calculating part for performing correction and calibration of an output value from the sensor to calculate a measurement value indicating the amount of each component and for calculating the device performance value from the measurement value, and a communicating part for transmitting the measurement value and the device performance value, which are calculated by the calculating part, to the device manager 6 according to a predetermined protocol.

The local computer further includes a mode control part 402 for receiving the command signal from the device manager 6 and controlling an operation mode (measurement mode, calibration mode, purge mode, etc.) and a status mode (sleep mode, standby mode, etc.) of the exhaust gas measuring devices 4, a calibrating part for calibrating the sensor, or a local storing part for storing device status information of the measuring devices 4 up to now, such as pump pressure information indicating a suction pressure of a built-in pump, sensitivity information related to the sensitivity of the sensor, accumulated operating time information indicating accumulated operating time of each part, and inspection date identifying information for identifying a predetermined inspection time and date of the measuring devices 4.

Figure 4:
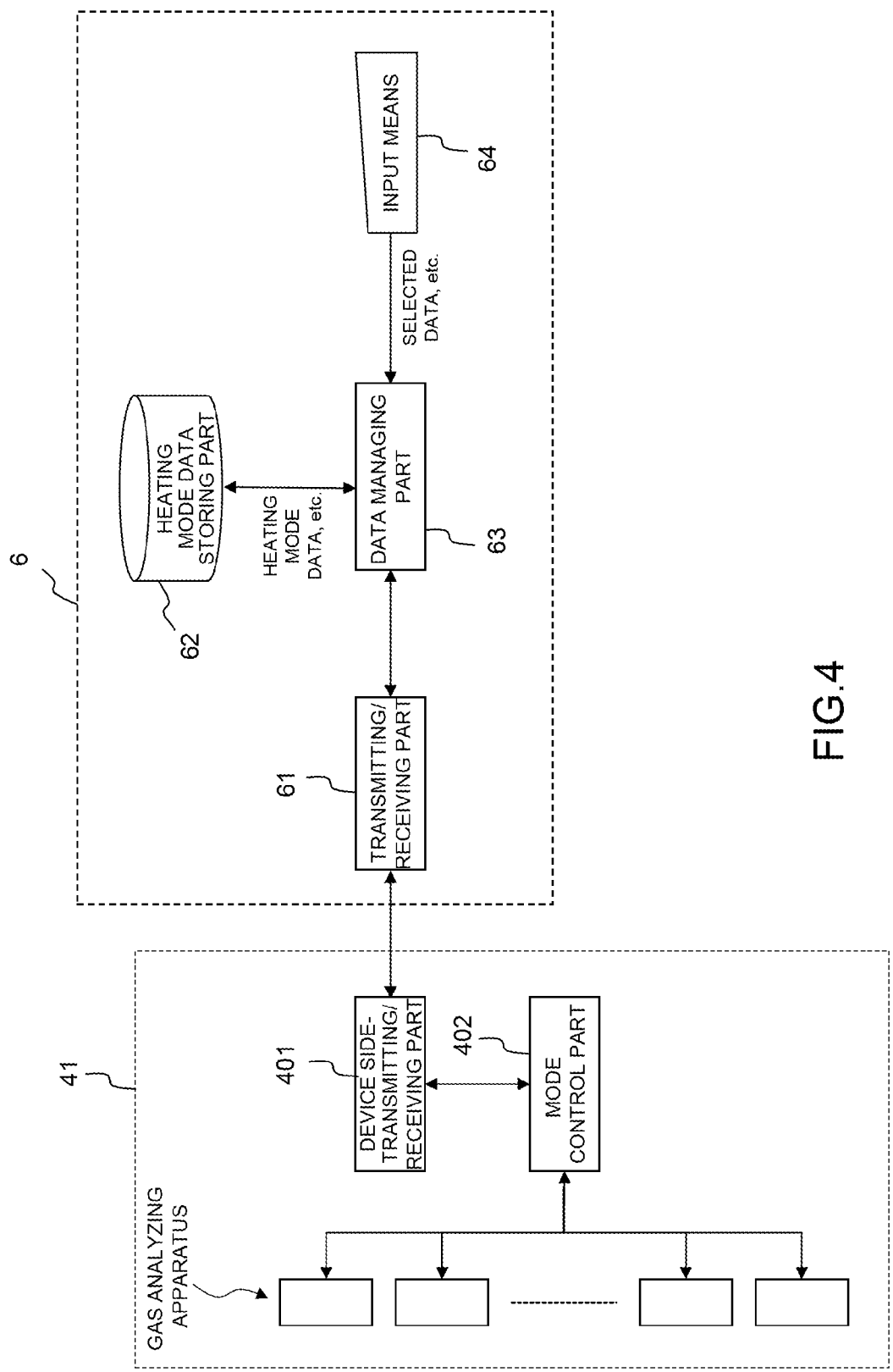
FIG. 4 is a functional block diagram of a device controller and the first measuring device (exhaust gas analyzing apparatus) in the embodiment.

As shown in FIG. 4, the local computer of the first measuring device 41 functions as a device-side transmitting/receiving part 401 and a mode control part 402.

The device manager 6 is configured by installing a predetermined program into, for example, a general-purpose computer, and physically includes a CPU, a memory, a display, an input means (keyboard, mouse, or the like) 64, and a communication interface. The CPU and peripheral devices cooperate according to the program stored in the memory such that the device manager 6 functions as a connection/disconnection monitoring part, a device indicator display part and a device information acquiring part, as shown in FIG. 4, in this embodiment as well as a transmitting/receiving part 61, a heating mode data storing part 62, and a data managing part 63. The device manager 6 is provided with a communication port, and the measuring devices 4 are connected to the device manager 6 so as to be intercommunicable in a wired or wireless manner.

Each part of the device manager 6 will be described below in detail.

The heating mode data storing part 62 is set in a predetermined area of the memory, and stores heating mode data indicating the heating state of each gas analyzer. As shown in FIG. 3, the heating mode data consists of four types of data (1) OFF mode data indicating that all of the hot hoses 413, 415 and the heaters 414, 416, and 417 are not operated, (2) sleep mode data indicating that the heaters 416, 417 for the analyzing part 412 are regulated to have the analyzable temperature (about 191° C. in this embodiment), while the hot hoses 413, 415 and the heater 414 for the sampling part 411 are not operated, (3) pause mode data indicating that the heaters 416, 417 for the analyzing part 412 are regulated to have the analyzable temperature, while the hot hoses 413, 415 and the heater 414 for the sampling part 411 are regulated to have the predetermined intermediate temperature (about 100° C. in this embodiment) that is lower than the analyzable temperature, and (4) standby mode data indicating that all of the hot hoses 413, 415 and the heaters 414, 416, and 417 are regulated to have the analyzable temperature (about 191° C. in this embodiment).

The data managing part 63 manages various types of data. For example, the data managing part 63 acquires the heating mode data selected by the operator or previously determined from the heating mode data storing part 62.

The transmitting/receiving part 61 is formed of a communication interface, and transmits the selected heating mode data to the first measuring device 41.

Next, a method of regulating the heating state of the first measuring device 41 having the above-mentioned configuration will be described.

First, the operator selects the heating mode on an initial screen (not shown) displayed on the display of the device manager 6 by use of the input means 64. Then, the data managing part 63 acquires the heating mode data selected by the operator from the heating mode data storing part 62.

Then, the transmitting/receiving part 61 transmits the heating mode data acquired from the data managing part 63 to the first measuring device 41.

The first measuring device 41 receives the heating mode data transmitted from the device-side transmitting/receiving part 401, and the mode control part 402 controls ON/OFF and temperatures of the hot hoses 413, 415 and the heaters 414, 416 and 417.

In this embodiment thus configured, by providing the sleep mode as the heating mode, the hot hose 413 for the exhaust gas introduction pipe L1, the hot hose 415 for the connection pipe L2, and the heater 414 for the sampling part 411 can be stopped while keeping the temperatures of the heaters 416, 417 for the analyzing part 412 to the analyzable temperature. Therefore, further energy saving can be achieved as compared to the case of using the conventional pause mode, and analysis can be rapidly performed by merely reheating the hot hose 413 for the exhaust gas introduction pipe L1, the hot hose 415 for the connection pipe L2, and the heater 414 for the sampling part 411.

The first aspect of the present invention is not limited to the above-mentioned embodiment.

In the embodiment, the heating mode data is stored in the device manager. However, the heating mode data may be held in the first measuring device (exhaust gas analyzing apparatus), and when the first measuring device is connected to the device manager, the device manager may read the heating mode data.

In the embodiment, the hydrogen flame ionization detector is shown as an example of the gas analyzer regulated to have the analyzable temperature in the sleep mode. However, the gas analyzer may be a CLD-type NOx meter.

The first aspect of the present invention may be variously modified without deviating from its subject matter.

<Second Aspect of the Present Invention>

Another embodiment of the present invention will be described below with respect to figures.

Figure 5:
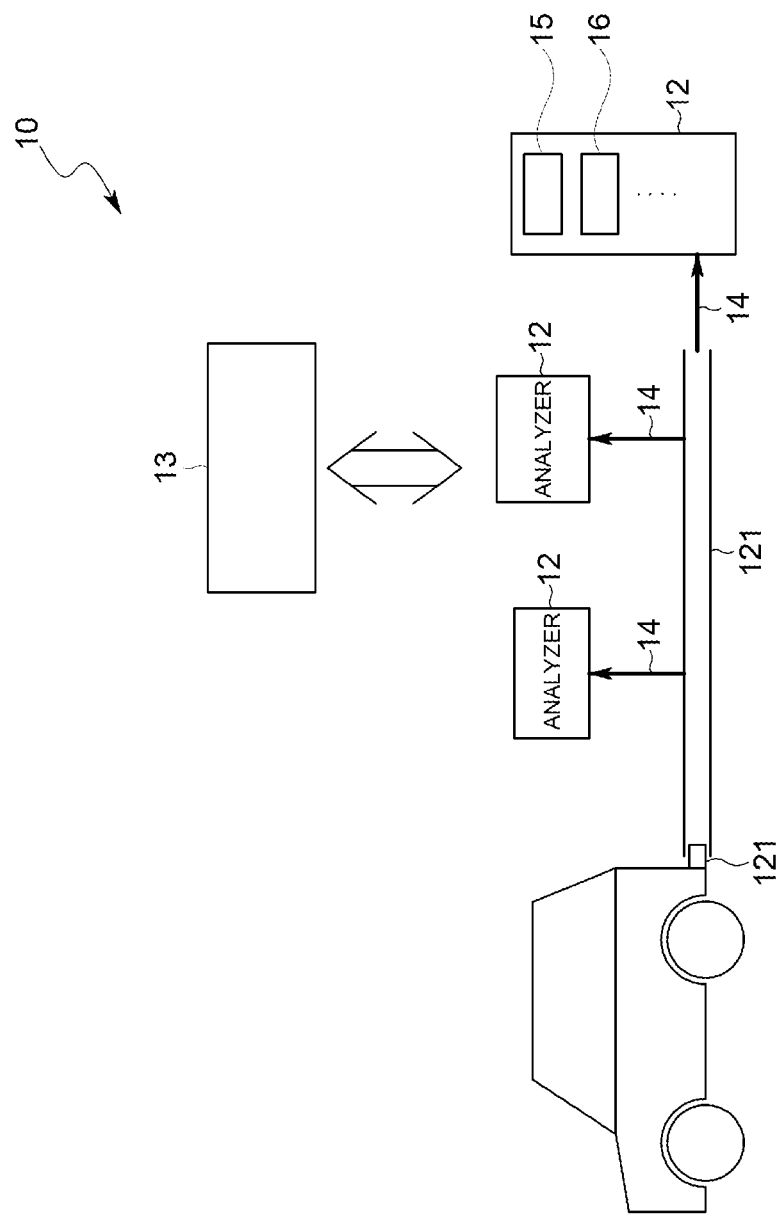
FIG. 5 is an overall configuration view of an analyzing system of a second aspect of the present invention.

As shown in FIG. 5, the exhaust gas analyzing system 10 in accordance with this embodiment serves to sample the exhaust gas of the automobile internal combustion engine, and analyze and calculate the component concentration and fuel consumption, and includes a plurality of exhaust gas analyzing apparatuses 12 and an information processor 13 for receiving and analyzing measurement data from each of the analyzing apparatuses 12 and controlling the operation of each of the exhaust gas analyzing apparatuses 12 to manage the apparatuses together.

Examples of the analyzing apparatuses 12 include a CVS apparatus and an EGR measuring apparatus, or an exhaust gas general analyzing apparatus having plurality of exhaust gas analyzing units 15, 16.

The exhaust gas general analyzing apparatus will be described herein in detail.

Figure 6:
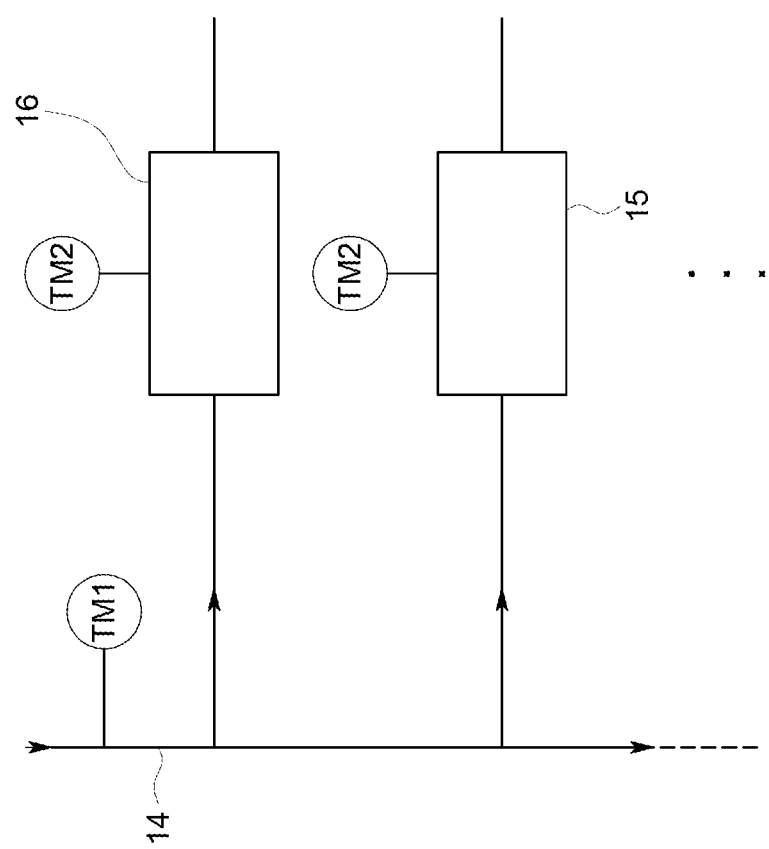
FIG. 6 is a configuration principle view of the exhaust gas general analyzing apparatus in the embodiment.

As shown in FIG. 6, the exhaust gas general analyzing apparatus includes an exhaust gas sampling line 14 for sampling the exhaust gas, a plurality of analyzing units 15, 16 for analyzing the exhaust gas introduced via the sampling line 14, and a temperature regulating mechanism for keeping temperatures of the analyzing units 15, 16 and the sampling line 14 at respective predetermined temperatures.

As the analyzing units 15, 16, the chemiluminescent nitrogen oxide analyzer 16 (hereinafter also referred to as chemiluminescent NO meter 16) and the hydrogen flame ionization detector 15 are provided.

Figure 7:
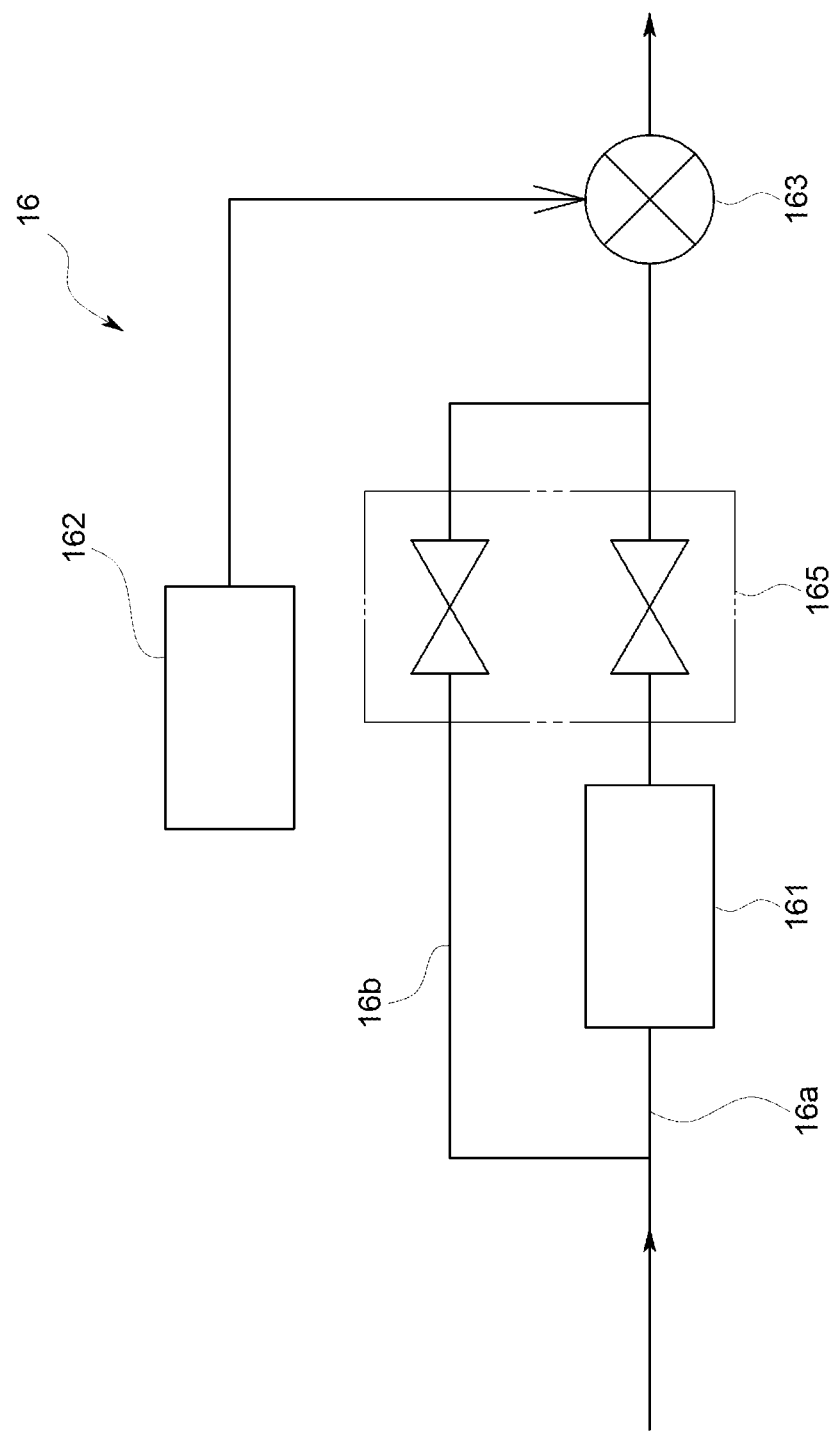
FIG. 7 is a configuration principle view of a chemiluminescent NO meter in the embodiment.

The chemiluminescent NO meter 16 measures the concentration of a nitrogen oxide contained in the exhaust gas. Specifically, as shown in FIG. 7, all $NO_x$ contained in the exhaust gas is converted into NO by an NO converter 161, and the NO is mixed with ozone as analyzing gas emitted from an ozone generator 162 in a reaction tank 163 to generate chemical reaction. A light detector (not shown) detects and outputs the intensity of light generated through this reaction. In this embodiment, a path 16a for guiding the exhaust gas to the reaction tank 163 through the NO converter 161 and a path 16b for guiding the exhaust gas directly to the reaction tank 163 are provided in parallel. Then, by selectively guiding the exhaust gas to the reaction tank 163 through either the path 16a or the path 16b by means of a valve 165, the concentration of only NO contained in the exhaust gas, as well as the concentration of $NO_x$ except for NO through taking a difference can be measured.

Figure 8:
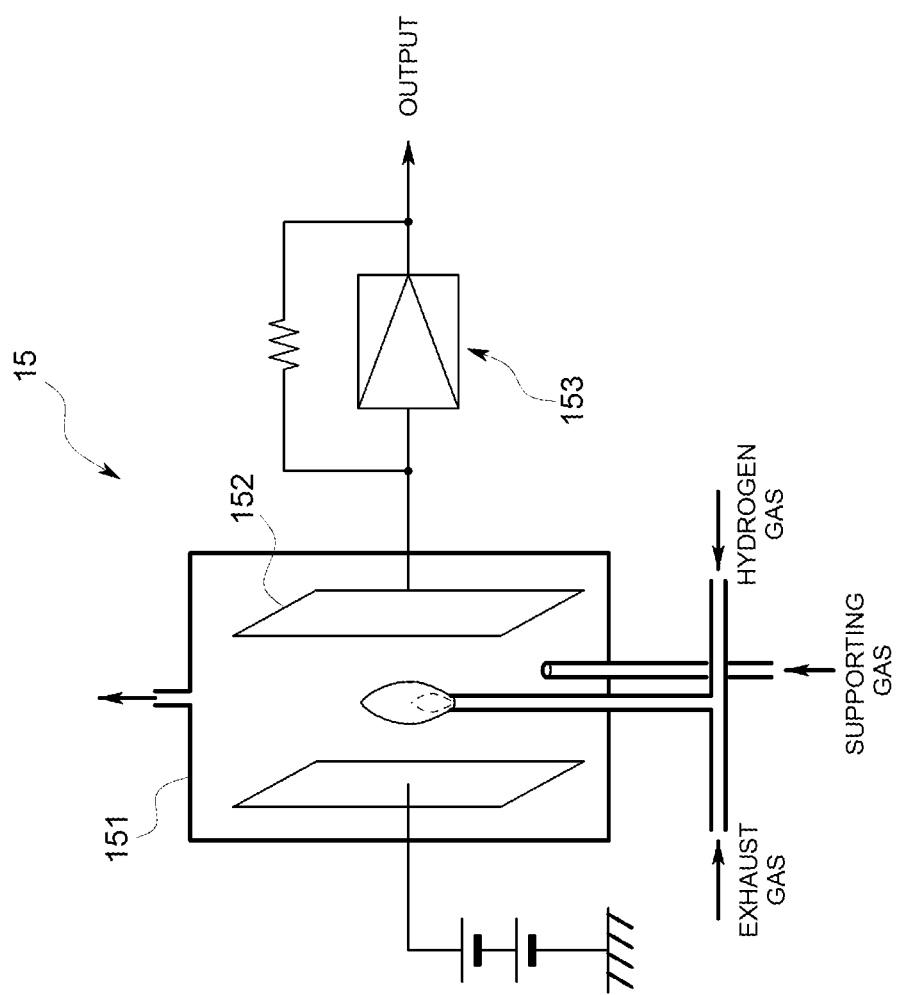
FIG. 8 is a configuration principle view of a hydrogen flame ionization detector in the embodiment.

As shown in a principle view in FIG. 8, in the hydrogen flame ionization detector 15, sampled exhaust gas is mixed with hydrogen gas as analyzing gas and supporting gas (air) at a certain ratio, the mixture is burned in a combustion chamber (chimney) 151 in the presence of an electric field, a current generated from ionized THC contained in the sample gas is collected by a collector 152, the current is amplified by an amplifier 153, and the amplified current is outputted. The amount (concentration) of THC can be calculated from the current value.

As shown in FIG. 6, the temperature regulating mechanism (not shown) includes heating means (not shown) such as a hot hose forming the sampling line 14 connecting the analyzing units 15, 16 to the exhaust gas pipe and a heater for heating equipment in the analyzing units 15, 16 and internal flow paths, and a heat-generation controller (not shown) such as a thermistor for controlling the heating value of the heating means, and controls the temperature of each target to be heated in the order of a thermometer TM1 provided in the sampling line and thermometers TM2 provided in the analyzing units 15, 16 by use of the heat-generation controller.

The information processor 13 serves to manage the analyzing apparatuses 12 as described above, and for example, in a state prior to the start of the analysis of the exhaust gas, can control the temperature regulating mechanism to set the analyzing apparatuses 12 to one of the heating modes: the "OFF mode", the "sleep mode", the "pause mode" and the "standby mode". The "OFF mode" refers to a state where the temperature regulating mechanism is not operated. The "sleep mode" refers to a state where main bodies (the reaction tank 163 of the chemiluminescent NO meter 16 and the chimney 151 of the hydrogen flame ionization detector 15) of the analyzing units 15, 16 are regulated to have the specified analyzing temperature (about 191° C. in this embodiment), while the temperatures of the hot hose and the internal flow paths of sampling line 14 are not regulated. The "pause mode" refers to a state where the main bodies of the analyzing units 15, 16 are regulated to have the specified analyzing temperature (about 191° C. in this embodiment), and the hot hose and the internal flow paths are regulated to have the predetermined intermediate temperature (about 100° C. in this embodiment) that is lower than the specified analyzing temperature. The "standby mode" refers to a state where the each part has the specified analyzing temperature and the exhaust gas can be immediately analyzed.

In the above-mentioned standby mode, the information processor 13 operates the temperature regulating mechanism, opens the predetermined valve so that the analyzing gas is introduced into the analyzing units 15, 16.

Specifically, when receiving a command to switch the heating mode to the standby mode from the operator or another apparatus, the information processor 13 starts to operate the temperature regulating mechanism immediately or after a certain period of time, obtains a required time taken until each part reaches a range of the specified analyzing temperature on the basis of a value of the thermometer TM1, TM2, and after the start of operation, obtains a temperature stabilizing time point that is a time point when the temperature regulated by the temperature regulating mechanism reaches the range of the specified analyzing temperature on the basis of the obtained required time, and starts to introduce the analyzing gas with a delay of a predetermined time from an operation start time point of the temperature regulating mechanism such that the temperature stabilizing time point substantially coincides with a stable-analysis enabling time point that is a time point when the analyzing units 15, 16 can start stable analysis after the start of the introduction of the analyzing gas.

Figure 9:
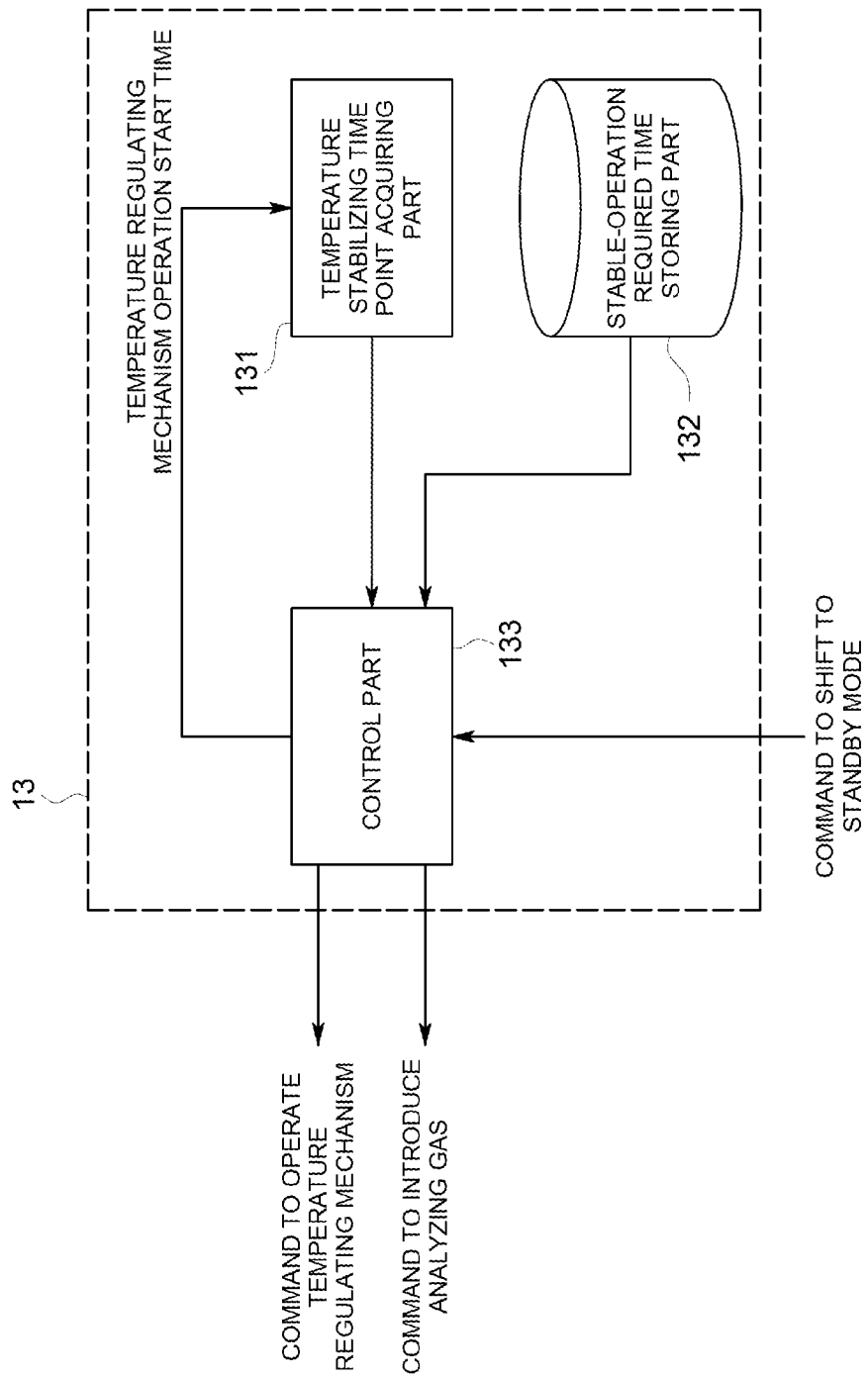
FIG. 9 is a circuit configuration view of an information processor in the embodiment.

Thus, as shown in FIG. 9, this information processor 13 has functions as a temperature stabilizing time point acquiring part 131, a stable-operation required time storing part 132, and a control part 133. These parts are acquired by operations of the CPU and peripheral devices according to the predetermined program stored in the memory.

Next, the information processor 13 will be described below in detail while describing the above-mentioned parts.

First, the control part 133 accepts the input of the standby mode command, and causes the temperature regulating mechanism to be in the standby mode.

Next, using the start of the operation of the temperature regulating mechanism as a trigger, the temperature stabilizing time point acquiring part 131 acquires the temperature stabilizing time point that is the time point when the temperature regulated by the temperature regulating mechanism reaches the range of the specified analyzing temperature from the operation start time point on the basis of the value of the thermometer TM1, TM2. Specifically, for example, the temperature stabilizing time that is the time point the temperature reaches the range of the specified analyzing temperature is previously stored in the memory for each temperature prior to the start of the operation, and the temperature stabilizing time is added to the operation start time point of the temperature regulating mechanism. The temperature stabilizing time stored in the memory is set to a value that varies according to the mode immediately before the standby mode.

Meanwhile, the control part 133 acquires a stable-operation required time previously stored in the stable-operation required time storing part 132 set in a predetermined area of the memory, that is, a required time taken until the analyzing units 15, 16 are put into a predetermined stable state in which the units can start stable analysis after the start of the introduction of the analyzing gas. The stable state refers to a state where gas in cells of the analyzing units is substituted and becomes stable.

Next, the control part 133 calculates an analyzing-gas introduction start time point by subtracting the stable-operation required time from the temperature stabilizing time point, and starts to introduce the analyzing gas at the calculated introduction start time point. The analyzing units 15, 16 may be validated or activated at an appropriate timing.

Figure 10:
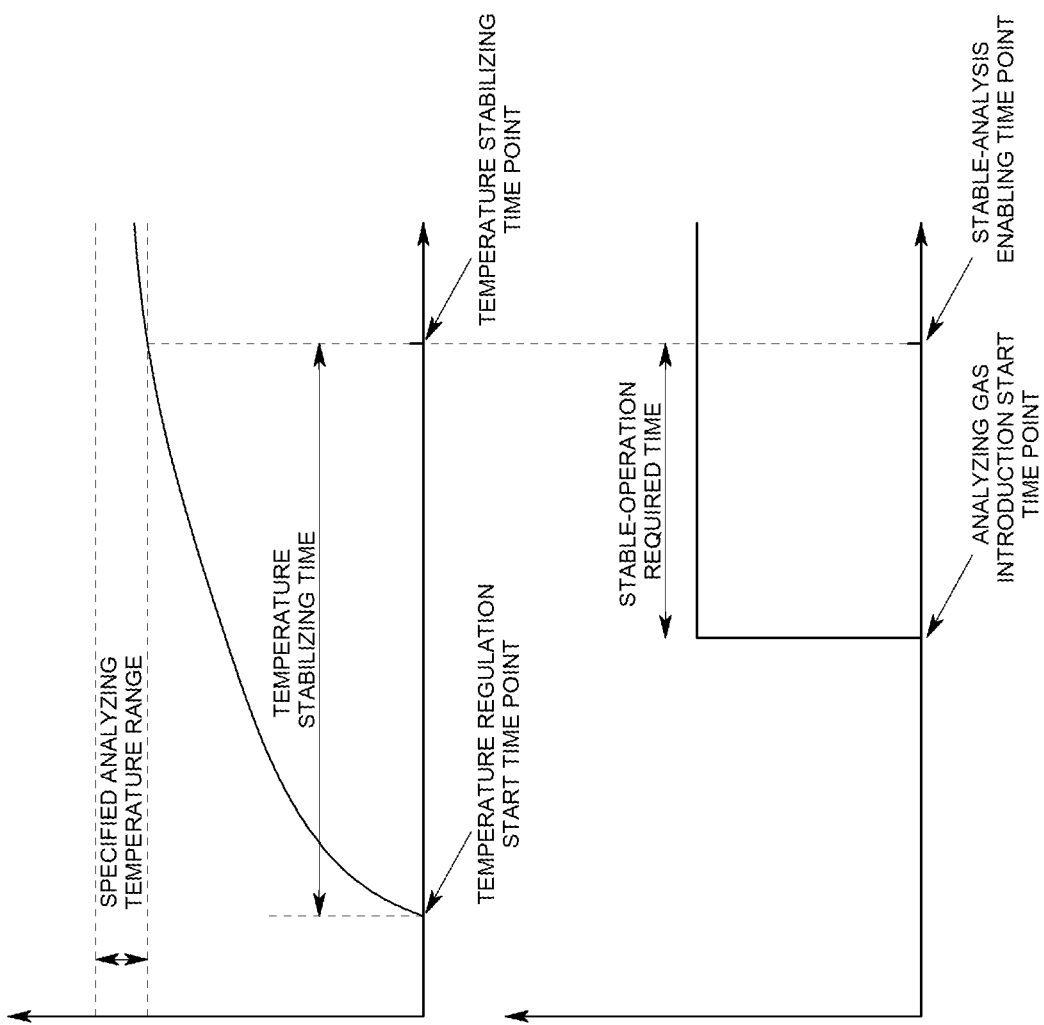
FIG. 10 is a timing chart showing an operation timing of temperature regulating mechanism and the introduction of analyzing gas in the embodiment.

As a result, as shown in FIG. 10, the stable-analysis enabling time point that is the time point when the analyzing units 15, 16 can start stable analysis after the start of the introduction of the analyzing gas coincides with the temperature stabilizing time point, shifting to the standby mode at the time point (standby completion time point).

In this embodiment thus configured, there never causes the case where the analyzing units 15, 16 is in the waiting state for temperature stabilization during the introduction of the analyzing gas and conversely, where the stabilization of the analyzing units 15, 16 after the introduction of the analyzing gas is waited in the temperature stable state. Therefore, consumption of the analyzing gas as well as power consumption of the temperature regulating mechanism before the standby state can be minimized.

The second aspect of the present invention is not limited to the embodiment.

For example, when there are the plural types of analyzing units 15, 16 as in the embodiment, the operation of the temperature regulating mechanisms of the analyzing units 15, 16 may be started upon the receipt of the standby mode command. However, the analyzing units 15, 16 may be different from each other in the temperature stabilizing time. In this case, one of the analyzing units 15, 16 may wait for completion of standby of the other of the analyzing units 15, 16, leading to energy loss. In such case, for example, the temperature regulating mechanism of one of the analyzing units 15, 16 with a longer time needed to achieve the standby mode may be operated first and with a delay of a certain period of time, the temperature regulating mechanism of the other of the analyzing units 15, 16 may be operated, such that the standby completion time points of the analyzing units 15, 16 coincide with each other.

The temperature stabilizing time point acquiring part 131 may calculate the temperature stabilizing time point from a temperature rise curve obtained by means of the temperature regulating mechanism.

Without the acquisition of the temperature stabilizing time point, for example, the analyzing gas may be introduced when the temperature regulated by the temperature regulating mechanism becomes a temperature that is lower than the specified analyzing temperature by a predetermined temperature. In this case, through a prior test, the predetermined temperature may be set such that a time elapsed until the predetermined temperature reaches the specified analyzing temperature is substantially equal to the stable-operation required time of the analyzing units 15, 16.

The stable-analysis enabling time point does not necessarily coincide with the temperature stabilizing time point accurately. Indeed, in this manner, both the consumption of the analyzing gas and the power consumption of the temperature regulating mechanism can be minimized. However, even when the stable-analysis enabling time point is slightly shifted from the temperature stabilizing time point, by at least introducing the analyzing gas after the start of the operation of the temperature regulating mechanism and before the temperature stabilizing time point, energy consumption can be reduced compared to that in conventional simultaneous-start case.

In the case where the temperature stabilizing time obtained by the temperature regulating mechanism is shorter than the stable-operation required time of the analyzing units 15, 16 from the introduction of the analyzing gas, the temperature regulating mechanism operation start time point may be delayed from the analyzing-gas introduction start time point.

The second aspect of the present invention is not limited to the embodiment, and may be variously modified without deviating from its subject matter.

REFERENCE SIGNS LIST

1: exhaust gas analyzing system
S1, S2: gas analyzer
L1: exhaust gas introduction pipe
L2: connection pipe
413, 415: hot hose
414, 416, 417: heater
402: mode control part
10: exhaust gas analyzing system
121: exhaust pipe
15, 16: analyzing units
14: exhaust gas sampling line
TM1, TM2: thermometer
131: temperature stabilizing time point acquiring part
132: stable-operation required time storing part
133: control part While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An exhaust gas analyzing apparatus comprising:
an analyzer main body for analyzing exhaust gas;
an exhaust gas introducing part for guiding the exhaust gas from an exhaust pipe passing the exhaust gas therethrough to the analyzer main body;
a heating arrangement for heating the analyzer main body and for heating the exhaust gas introducing part;
a temperature regulating mechanism for controlling the heating arrangement to regulate temperatures of the analyzer main body and the exhaust gas introducing part; and
a mode control part configured to select between a first mode which has the temperature regulating mechanism regulate the temperatures of the analyzer main body and the exhaust gas introducing part to an analyzable temperature that is a predetermined temperature allowing a start of analysis of the exhaust gas, and a second mode which has the temperature regulating mechanism regulate the temperature of the analyzer main body to the analyzable temperature and turning off a portion of the heating arrangement arranged to heat the exhaust gas introducing part.

2. The exhaust gas analyzing apparatus according to claim 1, wherein the mode control part is for further selecting a third mode which has the temperature regulating mechanism regulate the temperature of the analyzer main body to the analyzable temperature, and the exhaust gas introducing part to an intermediate temperature as a predetermined temperature, the predetermined temperature being lower than the analyzable temperature.

3. The exhaust gas analyzing apparatus according to claim 1, wherein the mode control part is for further selecting a fourth mode which has the temperature regulating mechanism turn off the heating arrangement.

4. An exhaust gas analyzing system comprising:
one or more analyzing units for analyzing exhaust gas sampled from an exhaust pipe of an internal combustion engine while using analyzing gas other than the exhaust gas;
a temperature regulating mechanism configured a regulate a temperature of the analyzing units and an exhaust gas sampling line; and
a control part configured to, prior to analysis of the exhaust gas, start introduction of the analyzing gas with a delay of a predetermined time from a start of the operation of the temperature regulating mechanism.

5. The exhaust gas analyzing system according to claim 4, wherein the introduction of the analyzing gas is started such that a temperature stabilizing time point as a time point when the temperature regulated by the temperature regulating mechanism reaches a predetermined stable temperature range for the first time after the start of the operation of the temperature regulating mechanism substantially coincides with an analyzable time point as a time point when the analyzing units can start stable analysis for the first time after the start of the introduction of the analyzing gas.

6. The exhaust gas analyzing system according to claim 4, wherein a hydrogen flame ionization detector using hydrogen gas as the analyzing gas and a chemiluminescent NO meter using ozone as the analyzing gas are adopted as the analyzing units.

7. An exhaust gas analyzing system comprising:
one or more analyzing units for analyzing exhaust gas sampled from an exhaust pipe of an internal combustion engine while using analyzing gas other than the exhaust gas;
a temperature regulating mechanism configured to regulate a temperature of the analyzing units and an exhaust gas sampling line;
a temperature stabilizing time point acquiring part for acquiring a temperature stabilizing time point as a time point when the temperature regulated by the temperature regulating mechanism reaches a predetermined stable temperature range for the first time after a start of the operation of the temperature regulating mechanism;
a stable-operation required time storing part for storing a stable-operation required time as a required time taken until the analyzing units are put into a predetermined stable state allowing the units to start stable analysis for the first time after a start of introduction of the analyzing gas; and
a control part configured to, prior to start of the exhaust gas, operate the temperature regulating mechanism, acquiring the temperature stabilizing time point from the temperature stabilizing time point acquiring part, acquiring the stable-operation required time from the stable-operation required time storing part, and calculating an introduction start time point of the analyzing gas such that a stable-analysis enabling time point when the analyzing units can start stable analysis for the first time after the start of the introduction of the analyzing gas substantially coincides with the temperature stabilizing time point.

8. An exhaust gas analyzing system comprising:
one or more analyzing units for analyzing exhaust gas sampled from an exhaust pipe of an internal combustion engine while using analyzing gas other than the exhaust gas;
a temperature regulating mechanism configured to regulate a temperature of the analyzing units and an exhaust gas sampling line; and
a control part configured to, prior to the start of the analysis of the exhaust gas, set an operation start time point of the temperature regulating mechanism and an introduction start time point of the analyzing gas such that a temperature stabilizing time point as a time point when the temperature regulated by the temperature regulating mechanism reaches a predetermined stable temperature range for the first time after the start of the operation of the temperature regulating mechanism substantially coincides with an analyzable time point as a time point when the analyzing units can start stable analysis for the first time after the start of the introduction of the analyzing gas.

* * * * *